(12) United States Patent
Solovyev

(10) Patent No.: US 9,744,196 B2
(45) Date of Patent: Aug. 29, 2017

(54) COMPOSITION FOR PARENTERAL ADMINISTRATION, METHOD FOR PRODUCING AND METHOD USE THEREOF

(71) Applicant: N2 PHARMACEUTICALS LTD, Manchester (GB)

(72) Inventor: Nikolay Vladimirovich Solovyev, Veliky Novgorod (RU)

(73) Assignee: N2 PHARMACEUTICALS LTD, Manchester (GB)

(*) Notice: Subject to any disclaimer, the term of this patent is extended or adjusted under 35 U.S.C. 154(b) by 38 days.

(21) Appl. No.: 14/694,290

(22) Filed: Apr. 23, 2015

(65) Prior Publication Data

US 2015/0224149 A1    Aug. 13, 2015

Related U.S. Application Data

(63) Continuation-in-part of application No. PCT/RU2013/000941, filed on Oct. 23, 2013.

(30) Foreign Application Priority Data

Oct. 24, 2014  (RU) ................ 2012145198

(51) Int. Cl.

| A61K 35/64 | (2015.01) |
|---|---|
| A61K 35/56 | (2015.01) |
| A61K 35/62 | (2006.01) |
| A61K 35/612 | (2015.01) |
| A61K 35/618 | (2015.01) |
| C12P 21/06 | (2006.01) |

(52) U.S. Cl.
CPC .............. A61K 35/62 (2013.01); A61K 35/56 (2013.01); A61K 35/612 (2013.01); A61K 35/618 (2013.01); C12P 21/06 (2013.01)

(58) Field of Classification Search
None
See application file for complete search history.

(56) References Cited

U.S. PATENT DOCUMENTS

| 2002/0187201 A1 | 12/2002 | Bhonde et al. |
|---|---|---|
| 2003/0044470 A1* | 3/2003 | Wani ............ A61K 35/618 424/547 |
| 2003/0148418 A1 | 8/2003 | Pyntikov et al. |
| 2004/0180025 A1* | 9/2004 | Long ............ A61Q 5/00 424/70.14 |
| 2009/0111747 A1 | 4/2009 | Ewart et al. |
| 2011/0124570 A1 | 5/2011 | Drieu La Rochelle et al. |

FOREIGN PATENT DOCUMENTS

| CN | 1112435 A | 11/1995 |
|---|---|---|
| CN | 1771997 A | 5/2006 |
| DE | 4309339 A1 | 9/1994 |
| EP | 1653981 B1 | 3/2013 |
| JP | 60058921 A | 4/1985 |
| JP | 2003024008 A | 1/2003 |
| JP | 2008037766 A | 2/2008 |
| JP | 2009035525 A | 2/2009 |
| KR | 20090024891 A | 3/2009 |
| KR | 20110001251 A | 1/2011 |
| KR | 20120049042 A | 5/2012 |
| RU | 2093046 C1 | 10/1997 |
| RU | 2098106 | 12/1997 |
| RU | 2134523 C1 | 8/1999 |
| RU | 2134571 C1 | 8/1999 |
| RU | 2221456 C1 | 1/2004 |
| RU | 2255747 C2 | 7/2005 |
| RU | 2259824 C2 | 9/2005 |
| RU | 2374891 C1 | 12/2009 |
| RU | 2384341 C1 | 3/2010 |
| RU | 2402320 C1 | 10/2010 |

OTHER PUBLICATIONS

Walsh et al. (2011) Animal Reproduction Science 123: 127-138.*
Coleman et al. (1985) J. Dairy Sci. 68: 1793-1803.*
Butler et al. (1989) J. Dairy Sci. 72: 767-783.*
Web document entitled: "What is a bivalve mollusk". Available at http://oceanservice.noaa.gov/facts/bivalve.html. Downloaded from website Jun. 2, 2016.*
Butler (2000) Animal Reproduction Science 60-61: 449-457.*
del Junco (1988) The relationship between rhematoid arthritis and reproductive function. ProQuest Dissertations and Theses.*
Lucy (2001) J. Dairy Sci. 84: 1277-1293.*
MacPhillamy (1963) Plant Science Bulletin, vol. 9, Issue 2, pp. 1-15.*
Phillipson (1999) Phytother. Res. 13, 2-8.*
Raskin et al. (2004) Current Pharmaceutical Design, 10, 3419-3429.*
Roche (2006) Animal Reproduction Science, 96: 282-296.*
International Search Report and Written Opinion Issued in PCT/RU2013/000941 dated Mar. 6, 2014, 12 pages.
Web-print http://www.yod.ru/drugs/id_125891.
Examination Report issued in corresponding GB application No. 1219111.0 dated Jan. 2, 2015, 5 pages.
Search Report issued in corresponding GB application No. 1219111.0 dated Feb. 21, 2013, 4 pages.
Office Action issued in corresponding EP application No. 13815861.3 dated Jun. 17, 2016, 7 pages.
Search and Examination Report issued in corresponding GB application No. 1506139.3 (which is divisional of GB 1219111.0), dated Jun. 24, 2015, 5 pages.

* cited by examiner

*Primary Examiner* — Chris R Tate
*Assistant Examiner* — Russell Fiebig
(74) *Attorney, Agent, or Firm* — Leason Ellis LLP

(57) ABSTRACT

The present invention relates to a field of veterinary and human medicine. In particular, the invention relates to a composition suitable for parenteral administration, based on hydrolyzate obtained from natural bioresources, a composition for use in treating and/or preventing a pathological condition in a mammal in need thereof, and various other uses thereof. More particularly the invention relates to a composition having immunomodulatory properties being based on a hydrolyzate obtained from bioresources, which composition is used for parenteral administration to a mammal in need thereof.

7 Claims, No Drawings

COMPOSITION FOR PARENTERAL ADMINISTRATION, METHOD FOR PRODUCING AND METHOD USE THEREOF

CROSS-REFERENCE TO RELATED APPLICATIONS

This application is a continuation-in-part of International application PCT/RU2013/000941 filed on Oct. 23, 2013 which claims priority benefits to Russian patent application RU 2012145198 filed on Oct. 24, 2012. Each of these applications is incorporated herein by reference for all purposes.

TECHNICAL FIELD

The present invention relates to the field of veterinary and human medicine. In particular, the invention relates to a composition suitable for parenteral administration, based on hydrolyzate obtained from natural bioresources, a method for producing said composition, a method of treating and/or preventing a pathological condition in a mammal in need thereof, using the above composition and various uses of said composition for treating and/or preventing purposes and other applications. More particularly the invention relates to a composition having immunomodulatory properties being based on a hydrolyzate obtained from bioresources, which composition is used for parenteral administration to a mammal in need thereof.

The present disclosure provides a composition for parenteral administration, based on a hydrolyzate obtained from bioresources. The composition comprises a wide variety of essential amino acids, melanoidins acting as antioxidants, regulatory peptides, saturated and unsaturated fatty acids, vitamins and micronutrient elements in a natural balanced ratio, having a number of useful properties and utilised in veterinary and medicine for the treatment and/or prophylaxis various diseases and conditions. In particular, it was surprisingly found that the composition for parenteral administration comprising 1-10% aqueous solution of the hydrolyzate obtained from the above-identified biological material for parenteral administration, has significant advantages as compared to compositions known in the state of the art. Moreover, a number of effects of the composition observable upon parenteral administration either do not appear upon oral intake of a pure hydrolyzate or appear after an extended period of time. On the other hand, said composition has also a number of advantages relative to known parenteral forms. Furthermore, it was found that parenteral intake of the composition disclosed herein is safe and does not provoke allergic reactions and other adverse effects.

BACKGROUND OF THE INVENTION

Various preparations and biologically active additives representing protein hydrolyzates obtained from source material of animal origin, in particular, sea products such as Mytilidae mussels and fish, meat of mammals and the like are known from the prior art. Said protein hydrolyzates usually represent bioadditives intended for oral administration, either individually or in combination with other preparations, as well as a food additive.

DE 4309339 discloses biologically active pharmaceutical product of natural origin, which comprises acid hydrolyzate of molluscs belonging to genus *Mytilus*, comprising amino acids, melanoidins and trace elements of edible mussel (*Mytilus edulis*) and Mediterranean mussel (*Mytilus gallo-provincialis*). In addition, the invention relates to various usages of the product. In particular, said product is used as a prophylactic, therapeutic radiopharmaceutical agent for humans and animals, has antipyretic properties and stimulates haemopoiesis, especially during radio- and chemotherapy.

Also known in the state of the art is the product MIGI-K (MIGI-K LP (МИГИ-К ЛП®), a liquid for oral administration, which represents a solution obtained by hydrolysis of Mediterranean mussels and used as a biologically active food supplement (see http://www.migiklp.ru).

Known in the art is a biologically active additive MIDEL (МИДЭЛ) having general tonic effect, close in properties to MIGI-K obtainable from White Sea mussels meat. Therapeutic and remedial administration of MIDEL combined with conventional treatment methods or as an individual preparation is recommended in immune deficiency conditions of various etiologies.

One of the disadvantages of oral hydrolyzates obtained from Mytilidae mussels meat is a relatively low rate of the development of desired effect upon daily administration.

Immunomodulatory compositions obtained from source material of animal origin other than mussels are also known in the state of the art.

RU 2221456 discloses a universal biologically active substance (BAS), which is a protein hydrolyzate obtained by a method comprising acid hydrolysis followed by neutralization of fish meat and protein containing by-products of animal or fish origin; filtering to provide a hydrolyzate and a residue; and subsequently drying the hydrolyzate. The claimed BAS is disclosed to be used as a food additive for animals, as a base for veterinary preparation, oral alimentation, perfume and beauty products, dairy products, confectionaries, etc.

Additionally, various preparations and compositions based on hydrolyzates derived from fish meat are known from EP 1653981, US 2009111747, US 2011124570.

RU 2402320 discloses a preparation comprising various amino acids, salts and micronutrient elements in a form of aqueous solution, as well as a method for preventing and correcting pathological conditions in animals, consisting in injectable administration of said preparation to an animal organism for prophylactic purposes 2 times a week over a month in a dose of 1.5-2.0 ml per 10 kg body weight, for treatment purposes in a dose of 3.0-5.0 ml per 10 kg body weight 2 times per 24 hours over 3-5 days in case of intoxication with synthetic and/or food poisoning in a 10-fold therapeutical dose. In particular, subcutaneous or intramuscular administration of said preparation provides more efficient prophylaxis and treatment of diseases of various etiologies. However, the production of said synthetic preparation is a tedious and energy-demanding process which comprises developing optimal qualitative and quantitative compositions of aqueous solutions of amino acids, vitamins, micro- and macroelements and glucose, in order to normalize metabolic processes in an animal organism, and preparation techniques thereof.

Various injectable preparations, such as, for example, evinton, are also known in the state of the art. Due to a combination of three homeopathic ingredients, evinton stimulates phagocytic activity and promotes barrier function of lymph nodes, skin, and mucous membranes as well as of other organs and tissues. Evinton is an immunomodulator used for treating diseases of bacterial and viral etiology such as canine distemper, panleukopenia, parvoviral enteritis, viral hepatitis, rhinotracheitis, etc. Evinton is administered daily, a mode of treatment lasting from a few days (for viral enteritis) up to 2-3 weeks (for viral hepatitis).

All the above-identified compositions have relatively low therapeutic and preventive efficiency. Beneficial effect upon oral administration of the preparations obtained from aquatic bioresources usually develops after a long period of time, provided that they are used in continuous manner. Oral preparations are used as biologically active food supplements, where the amount of preparation consumed over the entire course varies significantly and can be from tens of millilitres to a few litres. Moreover, the known injectable preparations do not possess broad spectrum of effects, probably due to their not sufficiently balanced composition, as in the case of, e.g., synthetically produced compositions, or, depending on their natural origin, as in the case of fish hydrolyzates, failing to comprise a full set of ingredients necessary and sufficient for achieving rapid preventive or therapeutic effect in human and animals.

Therefore, the present disclosure provides a composition having various therapeutic and preventive properties allowing one to achieve the desired positive effect within relatively short period of time regardless of a patient's ability and/or willingness to take food, ability and possibility of swallowing the composition and/or difficulties associated with its gastrointestinal uptake. Such composition may turn out to be particularly useful in veterinary medicine, where in many cases an animal suffering from a pathological condition or being in need of prophylactic agents for a certain disease, refuses to take food comprising oral preparation due to unpleasant taste and/or odour of the latter. The present composition solves this problem as well.

It was surprisingly found that properties of the composition disclosed herein include immunomodulatory activity, phagocytic activity, hepatoprotective activity, adaptogenic activity, antiherpetic activity, detoxifying activity, antiviral activity, and antibacterial activity, burn treating and wound healing properties. Moreover, said therapeutic effect can be achieved after the first few applications of the composition. In some cases therapeutic improvement is observable since the very first application of the present parenteral composition.

The present disclosure further provides a method for preparing the above-identified composition. Said method is simple in technique and its implementation does not require special manufacturing facilities and high professional skills, thereby contributing to its higher economic efficiency.

The composition for the parenteral administration is used in treating and/or preventing a pathological condition in a mammal in need thereof. That is to say, in other aspect the present disclosure provides a method of treating and/or preventing a pathological condition of various etiology in a subject in need thereof, the method comprising administering the above-identified composition. Said method includes an optimal dosage schedule for administering the composition, providing beneficial preventive and/or therapeutic effect while exhibiting no adverse effects irrespective of a subject's individual parametres; in particular not a single case of individual intolerance to the composition was observed in a mammal throughout clinical trial period.

Thus, the present disclosure provides an composition for parenteral administration, the composition comprising a hydrolyzate obtained from biological material of animal origin, methods for preparing said composition, the methods of treating and/or preventing a pathological condition in a mammal in need thereof using the composition described herein, and various other uses of said composition for medical and veterinary purposes.

SUMMARY

In a first aspect, the present disclosure provides a composition for parenteral administration to a mammal, comprising
1 to 10% wt of a hydrolyzate obtained from bioresources; and water.

The term "bioresources>> refers to any material of animal or plant origin used as a source for hydrolyzate. For example, animals and/or plants of marine or terrestrial origin can be used as a bioresource.

In one embodiment, the bioresources are selected from a group comprising bivalve molluscs, crustaceans, annelids and leeches. The bioresources are used for the production of the hydrolyzate with a balanced chemical constitution, including but not limited to a wide variety of amino acids such as essential amino acids, saturated and unsaturated fatty acids, melanoidins, carbohydrates, micro- and macroelements, the hydrolyzate being a basis for producing a composition which provides a desired therapeutic and preventive effect upon its parenteral administration to a mammal in need of such a treatment or prophylaxis.

The composition can comprise hydrolyzate, which is obtained from one or more species of source material. In particular, composition can comprise hydrolyzate obtained from bivalve molluscs, and/or crustaceans, and/or annelids, and/or leeches.

In one embodiment, the bivalve molluscs include floaters (*Anodonta*), *Unio* freshwater mussels, oysters (Ostreidae), true mussels (Mytilidae), tridacna (*Tridacna*), pearl-oysters (*Pinctada*), scallops (Pectinidae), shipworms (Teredinidae), geoduck (*Panopea abrupta*), ocean quahog (*Arctica Islandica*) and other harvested species of molluscs.

In one embodiment, crustaceans include krill, shrimps, crabs, langoustes, langoustines, crayfishes, lobsters and other harvested species. Preferably crustaceans include krill (*Meganyctiphanes norvegica*) and/or American lobster (*Homarus americanus*).

In another embodiment, the bioresource is a Red sea urchin (*Strongylocentrotus franciscanus*).

A composition having a number of prophylactic and therapeutic properties can be obtained from any of the above-identified bioresources. Furthermore, bivalve molluscs and crustaceans are common commercial primary products and therefore are commercially available bioresources for the production of the present composition. The qualitative and quiantitive contents of the hydrolyzate obtained from marine animal species can slightly vary depending on location and environmental conditions where the species are grown; however, major properties generally remain similar. Preferably, annelids and leeches are grown in invariable manufacturing environment, providing strictly constant formulation of the composition derived from these species. Alternatively, a composition according to the present invention can also be obtained from hydrolizate derived from marine bioresorces harvested from their natural environment.

The term "hydrolyzate obtained from bioresources", as used herein, refers to liquid solution obtained by hydrolysis of bioresources. According to one embodiment the hydrolizate has a dry matter content in a range from 1 to 20% by weight, preferably from 1 to 15% by weight, more preferably form 1 to 10% by weight, and most preferably form 1 to 5% by weight.

In one embodiment of the present invention, the hydrolyzate content in the composition is from 2 to 8% wt, preferably from 3 to 7% wt, more preferably from 4 to 6% wt, most preferably approximately 5% wt. In a further embodiment, the hydrolyzate content may vary from 1 to 4% wt, 1 to 3% wt, 1 to 2% wt, 6 to 9% wt, 7 to 9% wt and 8 to 9% wt. According to one embodiment the rest of the composition is water or isotonic solution suitable for injection into animal or human body. More specifically water may represent sterile water for injection.

In general, the hydrolyzate mass ratio does not preferably exceed 10% wt of the composition; otherwise the composition might not be suitable for some types of parenteral administration, in particular, for injectable administration, due to, for example, high salt concentration. On the other hand, the hydrolyzate weight ratio is usually kept not less than 1% wt in order to provide sufficient amount of components in the composition for desired effect in treating and/or preventing various conditions in a subject in need thereof.

In one embodiment, the hydrolizate can represent any product obtained from the above-identified bioresources suitable for oral consumption as a healthy food additive or feedstuff. More specifically, the hydrolyzate represents an orally consumed product extracted from bivalve molluscs, and/or crustaceans, and/or annelids, and/or leeches.

In one embodiment, the hydrolizate represents a commercially available nutrition product, food supplement or feedstuff produced from sea mussels, which is suitable for oral administration.

The term "a mammal/subject in need (of treatment or prophylaxis)" refers to any animal including *Mammalia*, or to a human, in need of treatment and/or prophylaxis of a pathological condition, disease, disorder, etc, or any other health condition, including healthy subjects, in need of health improvement.

In one embodiment, the mammal is an animal or human. Preferably the animal is a livestock animal selected from the group comprising cow, buffalo, yak, deer, pig, goat, sheep, rabbit, horse, donkey, camel, lama, sable, fox, mink, ferret and etc., or the animal can be a pet animal, such as dog, cat, rat, hamster, guinea pig, etc. In a further embodiment, the animal can be a wild animal living in wild nature conditions.

In one embodiment, "parenteral administration" comprises any ways of administration, except introduction of the present composition to a mammal in need thereof through gastrointestinal tract.

In one embodiment, the composition is an injectable composition. Said injectable administration can be performed intravenously (i.v.), intracutaneously, subcutaneously (s.c), intramuscularly (i.m.) or intraosseously. Surprisingly, it has been found that parenteral administration of the above composition significantly increases therapeutic, preventive and health improvement effects as compared to oral intake of undiluted (pure) hydrolyzate. Moreover, it considerably facilitates the development of such effects. Furthermore, parenteral administration of said composition allows achieving some effects which were not identified upon either oral administration of undiluted hydrolyzate derived from Mytilidae mussels' meat, or upon administration of the injectable forms, known in the prior art. It should also be noted that the composition had no adverse effects and does not cause allergic reactions upon regular parenteral administration according to clinical trials on animal models.

In a further embodiment, the composition can be formulated for topical administration that is applied to body surfaces such as the skin or mucous membranes to treat ailments via a large range of classes including but not limited to creams, foams, gels, lotions and ointments. In some embodiments, a topical formulation according to the invention can be epicutaneous, for application directly to the skin. In some embodiment, a topical formulation of the invention can be applied to the surface of tissues other than the skin, such as eye drops applied to the conjuctiva, or ear drops placed in the ear, or medications applied to the surface of a tooth. A topical effect achieved when using a topical formulation naccording to the present invention, in the pharmacodynamic sense, may refer to a local, rather than systemic, target for a medication. However, some other topically administered formulations according to the present invention may have systemic effects.

In particular, the composition can be formulated as an ointment, paste, liniment, cream, lotion, and other dosage forms, or other dosage forms suitable for topical application. The composition may be employed in skin application formulations, including, but not limited to cutaneous prolonged-action therapeutic system or transdermal patches. In particular, the disclosed composition can be applied to the thin skin body area of a mammal in need thereof. Furthermore, composition for external use may be used in treating open wounds, burns, frostbites, bruises, dislocations, fractures and other cutaneous and subcutaneous lesions.

In a further embodiment, the composition is characterized by amine nitrogen weight ratio of at least 0.01% wt. Preferably, the amine nitrogen weight ratio is 0.01 to 0.5% wt. More preferably, the amine nitrogen weight ratio is from 0.05 to 0.5% wt, most preferably from 0.02 to 0.1% wt. The amine nitrogen weight ratio characterizes the extent of the hydrolysis of the bioresources, and further represents a parameter indicating the completeness of the hydrolysis. The amine nitrogen weight ratio serves as an indirect measure of the presence of essential components in the final composition for parenteral administration.

In another embodiment, the composition provided herein has a pH value of 4 to 7, preferably 5 to 7, most preferably 5.5 to 6.5. A pH value within the said range indicates both sufficient neutralization of the hydrolyzate and suitability to use said composition for the treatment and/or prophylaxis of a mammal in need thereof.

In another embodiment, the composition provided herein has a dry matter content of 0.5 to 5% wt, preferably of 1 to 3% wt, most preferably of 1.2 to 1.8% wt based on the total weight of the composition.

In a further embodiment, the composition comprises a wide variety of amino acids depending on the type of bioresources used for producing thereof. In particular, the composition comprises amino acids, selected from a group comprising taurine, aspartic acid, threonine, serine, glutamic acid, sarcosine, glycine, alanine, valine, cystine, methionine, cystathionine, isoleucine, leucine, tyrosine, phenylalanine, β-alanine, γ-aminoisobutyric acid, γ-aminobutyric acid, ornithine, lysine, histidine, carnosine, arginine, oxyproline and proline. The composition may also comprise other amino acids.

In a further embodiment, the composition comprises at least one or more of human essential amino acids, selected from a group comprising valine, isoleucine, leucine, lysine, methionine, threonine, tryptophane, phenylalanine, arginine and histidine.

In one embodiment, composition comprises the following amino acids having the below specified mass ratios with respect to total amino acid content in said composition:
taurine 1 to 10%
aspartic acid 1 to 30%
glutamic acid, 1 to 30%
glycine 1 to 20%
alanine 1 to 10%
leucine 1 to 15%
phenylalanine 1 to 15% lysine 1 to 10%
arginine 1 to 20%
proline 1 to 50%
serine 1 to 10%
histidine 1 to 10%
threonine 0.5 to 10%
valine 0.1 to 10%
methionine 0.1 to 10%
isoleucine 1 to 10%

In one embodiment, the same composition may optionally have a dry matter weight ratio, pH value, amine nitrogen weight ratio and qualitative and quantitive amino acid content as indicated above.

In one embodiment, the composition disclosed herein is characterized by
amine nitrogen weight ratio of 0.01 to 0.5% wt, and/or
pH value of 4 to 7, and/or
dry matter weight ratio of 0.5 to 2% wt The composition disclosed herein comprises, along with amino acids, saturated and unsaturated fatty acids, selected from a group comprising acids with a long hydrocarbon chain having 12 to 25 carbon atoms. In particular, the composition preferably comprises one or more fatty acids, selected from a group comprising tridecyl acid C13:0, myristinic acid C14:0, tetradecenic acid C14:1, pentadecanoic acid C15:0, palmitic acid C16:0, palmitoleic acid C16:1, hexadecadienoic acid C16:2, hexadecapentanoic acid C16:5, heptadecanoic acid C17:0, heptadecenoic acid C17:1, heptadienoic acid C17:2, stearic acid C18:0, oleic acid C18:1, linolic acid C18:2, linolenoic acid C18:3, octadecatetraenoic acid C18:4, eicosenoic acid C20:1, eicosadienoic acid C20:2, eicosatrienoic acid C20:3, arachidonic acid C20:4, eicosapentaenoic acid C20:5, heptacosapentaenoic acid C21:5, docosanoic acid C20:0, docosadienoic acid C22:1, docosenoic acid C22:2, docosatetraenoic acid C22:4, docosahexaenic acid C22:6, tricosatetraenoic acid C23:4, tricosapentaenoic acid C23:5, tetracosenoic acid C24:1.

In other embodiment, the composition comprises micronutrient elements such as potassium, calcium, magnesium, iron, zink, copper, cadmium, manganese, nickel, chrome, selenium, iodine.

The composition may additionally comprise biologically active additives, which are known in the state of the art; agents and preparations for preventing and treating pathological conditions, diseases and disorders in humans and animals, known in the field of veterinary and medicine; macro- and micronutrient elements, amino acids, melanoidins, carbohydrates, peptides and vitamins. Preferably, said composition is supplemented with appropriate salts to produce physiological solution, suitable for parenteral administration. In one embodiment of the invention, said composition is admixed with glucose prior to administration.

In a second aspect, the present disclosure provides a method for producing a composition for parenteral administration to a mammal in need of prophylaxis and/or treatment. In particular, herein disclosed to method for producing composition for parenteral administration to a mammal, including:

(a) an enzymatic hydrolysis and/or acid hydrolysis of bioresources selected from a group comprising bivalve molluscs, crustaceans, annelids and leeches, to provide a first solution;

(b) filtering the first solution to provide a second solution;

(c) mixing the second solution with water to provide a composition comprising from 1 to 10% wt of the second solution.

In one embodiment, step (a) includes enzymatic and acid hydrolysis. Any enzymes of animal, plant or microbial origin can be used. In particular, said enzymes include without limitation protomegaterin, protakrin, protosubtilin, trypsin, pepsin and other interchangeable enzymes. The amount of enzyme, pH value, temperature and other conditions are selected empirically, depending on the type of enzyme and source material subjected to enzymatic hydrolysis. pH value during enzymatic hydrolysis is maintained between 1 and 12, more preferably between 1 and 10, most preferably between 1 and 9. Temperature during enzymatic hydrolysis is maintained between 20 and 80° C., more preferably between 30 and 70° C., most preferably between 30 and 60° C. An enzyme is added to a source material as a dry powder, while stirring. Said step does not require additional fresh water supply, and can be carried out at the sites of harvesting of said source material. Enzymatic hydrolysis is carried out over 10 min to 5 hours, preferably over 20 min to 3 hours, most preferably over 30 min to 1 hour.

Where said biological material is a bivalve mollusc, enzymatic hydrolysis may be needed for loosening of the mollusc adductor muscle, thereby permitting separation of molluscs' soft tissues and shells, and for primary hydrolysis of the molluscs' soft tissues. Once the acid hydrolysis is finished, the molluscs' shells are separated from soft tissues by filters such as vacuum filter or press filter, and/or vibration screen. Separation of soft tissue is followed by acid hydrolysis or further enzymatic hydrolysis with one or more enzymes.

Alternatively, valves and shells of bivalve molluscs can be detached physically by hand and/or by methods employing no enzymatic means, for instance, by hot vapour. Bivalve molluscs can also be crushed and acidolysed without the use of enzymes.

Source materials other than bivalve molluscs such as crustaceans, in particular krill, as well as leeches and annelids, may also be subjected to enzymatic hydrolysis.

In one embodiment, acid hydrolysis of the source material is either following enzymatic hydrolysis or performed instead of it. Acid hydrolysis is performed using an acid selected from a group comprising common acids such as sulphuric and/or hydrochloric acid, as well as other interchangeable mineral acids and organic acids. Acid hydrolysis takes approximately 10 to 30 hours, more preferably 12 to 27 hours, most preferably 14 to 24 hours. Duration of the hydrolysis depends on the amount and type of the source material, as well as on its degree of processing prior to acid hydrolysis. Generally, enzymatic hydrolysis promotes the reduction of subsequent acid hydrolysis duration by approximately 3-7 hours.

In one embodiment, the amount of acid employed in the acid hydrolysis is between 5 to 20% wt, preferably 5 to 15% wt, more preferably 5 to 10% wt with respect to the amount of source material being processed. Said amount of acid is generally sufficient for the hydrolysis process to be entirely completed. However, the amount of acid may be selected empirically, depending on the type of biological resource and the extent of hydrolytic conversion.

In one embodiment, the temperature for acid hydrolysis is adjusted in the range of between 80 to 120° C., preferably between 90 to 110° C., most preferably between 95 to 105° C. In particular, acid hydrolysis is carried out while the solution is boiling.

According to one embodiment, acid hydrolysis is carried out in a glazed or glass reactor equipped with a thermometer or thermocouple for temperature control, and with a stirring device.

Alternatively, feed source material may not be subjected to acid hydrolysis where it is unnecessary. In particular, completeness of the hydrolysis can be achieved by the enzymatic hydrolysis only. Whether the acid hydrolysis has been carried out, the next step is a step of neutralization of the first solution, including adding a neutralizing agent to the first solution in an amount, sufficient for adjusting pH value of the solution from 4 to 7, preferably 5 to 7, most preferably 5.5 to 6.5. Agents that produce water and neutral salt, for example, bases such as NaOH and/or KOH in solid form, or a solution thereof, as well as basic salts and solutions thereof, are used as neutralizing agents. In particular, sodium or potassium carbonates and/or hydrocarbonates can be employed as a salt. Preferably neutralizing agent is a solid sodium hydroxide.

According to one embodiment, filtration of the obtained first solution is further performed to give the second solution.

In one embodiment, a step of filtration of the first solution is preceded by its stroring at the temperature of 1 to 25° C., preferably of 4 to 15° C., most preferably of 4 to 6° C. for at least 10 days, preferably from 10 to 20 days, most preferably from 10 to 30 days. This step provides a more complete sedimentation of the insoluble components of the first solution and their separation during the next step, thereby increasing stability of the final composition for parenteral administration.

After storing, the residue is separated to provide the second solution. The step of filtering the first solution to provide the second solution is performed by using mechanical filters, preferably vacuum filters. Said step may be subdivided into several steps and may include hot filtering the first solution after completed enzymatic and/or acid hydrolysis, as well as one or more repetitive steps of filtering the cooled first solution to provide the second solution. Preferably, the step of filtering is carried out after the step of storing the first solution under above specified conditions.

The next step comprises admixing the second solution with water to give a composition comprising from 1 to 10% wt of the second solution, preferably 2 to 8% wt, or 3 to 7% wt, more preferably 4 to 6%, most preferably approximately 5% wt. In a further embodiment, weight content of the second solution may be from 1 to 4% wt, 1 to 3% wt, 1 to 2% wt, 6 to 9% wt, 7 to 9% wt and 8 to 9% wt. Said water is a distilled water, or sterile water for injection. The second solution weight content in the composition corresponds to the amount required for the production of a final composition which is suitable for parenteral administration, in particular, for intravenous administration. In one embodiment, the resulting composition is isotonic to the blood of a mammal in need of prophylaxis or treatment with said composition. The composition may be admixed with an ingredient selected from a group comprising vitamins, carbohydrates, additional amino acids, micro- and macroelements, glucose and the like, prior to its administration.

In other embodiments, after the addition of distilled water and/or water for injection, the composition is sterilized and loaded into storage containers. Ampoules, flacons, bottles, bags and the like can be used as storage containers for the composition. The production method is performed under aseptic conditions in compliance with all the requirements stipulated by the State Pharmacopoeia for particular parenteral forms. Containers with the final composition are stored at the temperature of 0 to 25° C., preferably of 4 to 6° C. A shelf life of the composition upon appropriate conditions may last for at least 2 years. Preferably, if all the above-identified conditions are observed, the composition remains stable and suitable for use for 5 years and more.

In a third aspect, the composition is used in treating and/or preventing a pathological condition in a mammal in need thereof, wherein the composition is administered parenterally to a subject in need thereof. Alternatively, in a third aspect the present invention relates to a use of the composition for treating and/or preventing a pathological condition in a mammal in need thereof.

In another embodiment, the present invention provides a method of treating and/or preventing a pathological condition in a mammal in need thereof, including parenteral administration of said composition to a mammal in need of such a treatment or prophylaxis.

In one embodiment, the present invention relates to a use of the composition for treating and/or preventing a pathological condition in a mammal in need thereof including parenteral administration of said composition to a mammal in need of such treatment or prophylaxis.

Said parenteral administration includes any mode of administration which does not involve introduction of said composition into a mammal body through organs of gastrointestinal tract. In particular, the parenteral administration may be an injectable administration, selected from a group comprising subcutaneous injectable administration, intracutaneous injectable administration, intramuscular injectable administration, intravenous injectable administration or intraosseously injectable administration. Said parenteral administration can also be an external application of the above-identified composition.

In one embodiment, the composition is administered in an amount of 0.05 ml/kg to 10 ml/kg of a body weight of said mammal for 1-5 times per 24 hours over 1 to 50 days. More preferably, composition is administered in an amount of 0.1 to 1 ml/kg over 1-15 days.

In another embodiment, the composition is administered once in an amount of 0.05 ml/kg to 10 ml/kg of a body weight of said mammal every 1-5 days in an amount of 0.05 to 10 ml/kg over 1 to 50 days. More preferably, the composition is administered in an amount of 0.1 to 1 ml/kg over 1-15 days.

In another embodiment, the composition is optionally applied once in 45-120 days over a year in an amount of 0.05 ml/kg of a body weight to 10 ml/kg of a body weight of said mammal. More preferably, composition is administered in an amount of 0.1 to 1 ml/kg once in 90 days.

Furthermore, a regime of administration of the composition can be adjusted according to the type of pathological condition and general well-being of a mammal in need thereof, or according to specific purpose of said composition.

In one embodiment, said pathological condition, which is treated and/or prevented, is a liver injury of various etiology, hepatosis, organism intoxication, skin disease, hair disease, dermatitis, skin integument discontinuities due to wounds or burns, obstructive pulmonary diseases, pneumonia, acute respiratory viral infection (ARVI), influenza virus, circovirus infection, acidosis, herpes, stress condition, postoperative weakness, inflammatory processes affecting intestinal mucous membranes, osteodystrophy, rickets-like conditions, arthrosis, osteochondrosis, atherosclerosis and other diseases.

In another embodiment, the composition is useful for fast and effective immunity improvement, normalization of metabolism, in particular calcium-phosphorus metabolism, body weight gain, where necessary, and loss of overweight, increasing liver protein synthetic ability; as a wound-healing and burns healing promoting agent; as an agent delaying benign and malignant tumor growth; as a hair growth stimulating agent; as an agent for inducing estrus in livestock animals and improving reproductive function in animals.

In one embodiment, the composition is used in any intoxications, e.g., in particular, intoxications of exogenous and endogenous origin. Therefore, the composition is used as a detoxifying agent, wherein the composition is administered as a single dose in an amount of 0.1 to 10 ml/kg of a body weight of a mammal in need thereof. In most cases a mammal in need thereof gets rid of intoxication symptoms upon administration of a dose between 0.1 to 0.5 ml/kg. In case of poisoning symptoms recurrence, the composition is administered 1 to 5 times in similar doses.

According to one embodiment the present disclosure relates to a method of detoxifying a mammal in need thereof by administering via injection to said mammal a composition comprising about 1 to 10% wt of the hydrolyzate, obtained by enzymatic hydrolysis and/or acid hydrolysis from bioresources, said bioresources selected from a group comprising bivalve molluscs, crustaceans, annelids and leeches, and water.

In another embodiment, the composition is used for boosting the immune status of a mammal in need thereof. In other words, said composition is an immunomodulatory composition. In particular, the composition is used to cure weakness of the body resulting from various diseases, and also where a mammal is attenuated, e.g., due to previous treatment with antibiotics and/or immunosuppressive agents. For example, the composition is administered to a mammal in need of rehabilitation during postoperative or post-chemotherapy period, or during post-pregnancy period, feeding offspring and etc. During epidemic of infectious diseases such as influenza, acute respiratory virous infections and other diseases, the composition is administered as a prophylactic agent.

In another embodiment, the composition is used for the normalization of metabolism in a mammal in need thereof. In this case, normalization of the metabolism is indirectly assessed, in addition to key parameters estimation, by increased or reduced body weight in a mammal in need of such an increase or reduction, respectively; augmentation of hair or wool coat covering, improving mobility and overall activity of senior animals; and by other parameters.

In another embodiment, the composition is used for the normalization of calcium-phosphorus metabolism in a mammal in need thereof. In this case, normalization of calcium-phosphorus metabolism is assessed by calcium and phosphorus content in a mammal organism.

In another embodiment, the composition is used for estrus induction in an animal and for general improvement of the animal's reproductive function.

According to one embodiment the present disclosure relates to a method of improving reproductive function of a mammal in need thereof by administering via injection to said mammal a composition comprising about 1 to 10% wt of the hydrolyzate, obtained by enzymatic hydrolysis and/or acid hydrolysis from bioresources, said bioresources selected from a group comprising bivalve molluscs, crustaceans, annelids and leeches, and water.

In particular, it was found that intramuscular administration of 1 to 3 doses of the composition in an amount of 0.005 to 1 ml/kg, preferably 0.01 to 0.1 ml/kg, more preferably 0.01 to 0.05 ml/kg of animal body weight, to livestock animals during 24 hours prior to fertilization, allows the above effect to be achieved. In particular, achievement of the above effect was observed upon intramuscular administration of the composition to cows in an amount of 0.01 to 0.05 ml/kg twice over 24 hours.

In another embodiment, the composition is used for reducing stress in a mammal in need thereof. In particular, it was shown in experimental models on animals that the composition exhibits a number of adaptogenic/antistress properties. For example, the composition was shown to improve survival and to increase postnatal performance in pigs, and also gave positive results in the model of transport stress in horses.

According to another embodiment the present disclosure relates to a method of reducing stress in a mammal in need thereof.

In another embodiment, the composition is used as a wound healing agent in a mammal in need thereof, wherein said wounds may occur as a result of various physical injuries, in particular skin integument discontinuities, as well as various diseases such as dermatitis, psoriasis, herpes and other lesions of skin integument of various etiology.

According to another embodiment the present disclosure relates to a method of healing wounds in a mammal in need thereof.

In another embodiment, the composition is used as a growth-promoting agent in a mammal. In particular, growth-promoting effect of said composition was estimated by weight gain figures in livestock animals treated with the composition relative to the control group of animals, not treated with the composition or only treated with hydrolyzate administered orally.

In one embodiment the composition is used for treating oedema of various etiology.

In one embodiment the composition is used for treating and/or preventing a pathological condition selected from a group comprising atherosclerosis, hypertonic disease, coronary insufficiency, myocardial infarction in the acute phase and later in the recovery phase, kidney failure, hereditary and acquired metabolic disorders (dyslipidemia etc.), thrombosis and thrombophlebitis, endocrine age-related disorders, nonrespiratory pulmonary pathology (asthma), stroke, chronic heart disease, vegetative vascular dystonia, rheumatoid arthritis, urinary stone disease, haematuria of various origin, vasculitis, psoriasis, burns and ulcers, dermatitis, neurodermatitis, eczema, atopic dermatitis, ocular burns, type II diabetes, consequences of type I and II diabetes mellitus, lupus erythematosus, rheumatoid arthritis, autoimmune glomerulonephritis, myasthenia, osteochondrosis vertebralis, degenerative joint disease, osteoporosis, arthrosis, arthritis, hip dysplasia, gout, coxarthrosis, fractures, trauma and trauma consequences, muscular dystrophy, secondary immunodeficiency of various etiologies, immunodeficiency due to chemotherapy of cancer, gastroduodenitis, gastric andduodenal ulcer, colitis of different origin, intestinal andbiliary dyskinesia, pancreatitis, disbacteriosis, Crohn's disease.

It should be appreciated that the above-mentioned expression "a composition is used for < . . . >" has substantially the same meaning as "use of a composition for < . . . >".

According to one embodiment the present disclosure relates to a method of treating and/or preventing an above-identified pathological condition.

These and other advantages of the present invention are illustrated in more detail by specific examples in the detailed description that is set forth herein below.

DETAILED DESCRIPTION

Production of the Composition for Parenteral Administration

EXAMPLE 1

100 kg of ocean quahog (*Arctica Islandica*) was placed into fermenter, and upon continuous mechanical stirring the apparatus was heated with hot water to 42° C. 1 kg of protosubtilin was added to the fermenter. pH was adjusted to neutral reaction according to pH-meter readouts. Enzymatic hydrolysis was carried out for 40 minutes upon continuous stirring, and then valves were separated by mechanical screening. The resulting solution was supplemented with concentrated hydrochloric acid and underwent acid hydrolysis over 16 hours in a glazed stirred-tank reactor at the temperature of 100-105° C. Upon completion of the hydrolysis process, the resulting solution was vacuum pumped into neutralizing tank, cooled by water circuit and neutralized with a dry alkali to pH value falling in the range of 4-6, while continuous cooling. The neutralized hydrolyzate was stored to settle for 15 days at the ambient temperature of 20° C. Further, vacuum filtration was performed to separate the resulting residue, thereby producing a hydrolyzate solution without solids. The resulting hydrolyzate solution weighting approximately 10 kg was supplemented, upon stirring, with the required amount of distilled water (<<water for injection>>), to provide a solution containing 5% wt of the hydrolyzate. Prior to filling containers with the end-use composition, the composition was subjected to thermal sterilization, followed, where appropriate, by filtration of the solution. Containers with the final composition were stored at the temperature of 4-6° C., out of direct sunlight. Results of chemical examination of the obtained composition are given below.

an amine nitrogen weight ratio is 0.08%
a dry matter weight ratio is 1.5% wt
a pH value is 5.7

Micronutrient elements (qualitative composition):

1. Potassium
2. Calcium
3. Magnesium
4. Iron
5. Zink
6. Copper
7. Cadmium
8. Manganese
9. Nickel
10. Chrome
11. Selenium
12. Iodine Amino acid content
(including essential amino acids) Fatty acids (lipids)

| Amino acid | Fatty acids (lipids) |
|---|---|
| 1. Taurine | 1. Tridecyl acid C 13:0 |
| 2. Phosphoethanolamine | 2. Myristinic acid C 14:0 |
| 3. Aspartic acid | 3. Tetradecenic acid C 14:1 |
| 4. Threonine | 4. Pentadecanoic acid C 15:0 |
| 5. Serine | 5. Palmitic C 16:0 |
| 6. Glutamic acid | 6. Palmitoleic C 16:1 |
| 7. Sarcosine | 7. Hexadecadienoic C 16:2 |
| 8. Glycine | 8. Hexadecapentanoic C 16:5 |
| 9. Alanine | 9. Heptadecanoic C 17:0 |
| 10. Valine | 10. Heptadecenoic C 17:1 |
| 11. Cystine | 11. Heptadienoic C 17:2 |
| 12. Methionine | 12. Stearic C 18:0 |
| 13. Cystathionine | 13. Oleic C 18:1 |
| 14. Isoleucine | 14. Linolic C 18:2 |
| 15. Leucine | 15. Linolenoic C 18:3 |
| 16. Tyrosine | 16. Octadecatetraenoic C 18:4 |
| 17. Phenylalanine | 17. Eicosenoic C 20:1 |
| 18. β-alanine | 18. Eicosadienoic C 20:2 |
| 19. γ-aminoisobutyric | 19. Eicosatrienoic C 20:3 |
| 20. γ-aminobutyric | 20. Arachidonic C 20:4 |
| 21. Ethanolamine | 21. Eicosapentaenoic C 20:5 |
| 22. Ornithine | 22. Heptacosapentaenoic C 21:5 |
| 23. Lysine | 23. Docosanoic C C 20:0 |
| 24. Histidine | 24. Docosadienoic C 22:1 |
| 25. Carnosine | 25. Docosenoic C 22:2 |
| 26. Arginine | 26. Docosatetraenoic C 22:4 |
| 27. Oxyproline | 27. Docosahexaenic C 22:6 |
| 28. Proline | 28. Tricosatetraenoic C 23:4 |
| | 29. Tricosapentaenoic C 23:5 |
| | 30. Tetracosenoic C 24:1 |

EXAMPLE 2

50 kg of krill (*Meganyctiphanes norvegica*) was placed into reactor upon continuous stirring and supplemented with concentrated hydrochloric acid. Acid hydrolysis was carried out for 24 hours in a glazed stirred-tank reactor at the temperature of 100-105° C. Upon completion of the hydrolysis process, the resulting solution was vacuum pumped into neutralizing tank, cooled by water circuit and neutralized with a dry alkali to pH value being in the range from 4 to 6, while continuous cooling. The neutralized hydrolyzate was stored to settle for 20 days at the ambient temperature of 20° C. Further, vacuum filtration was performed to separate the resulting residue, thereby producing a hydrolyzate solution without solids. The obtained hydrolyzate solution was supplemented with the required amount of distilled water (<<water for injection>>) while stirring, to provide a solution containing 5% wt of the hydrolyzate. Prior to filling containers with the end-use composition, the composition was subjected to thermal sterilization, followed, where appropriate, by filtration of the solution. Containers with the final composition were stored at the temperature of 4-6° C., out of direct sunlight. Chemical analysis of the obtained composition is given below.

an amine nitrogen weight ratio is 0.10%
a dry matter weight ratio is 0.8% wt
a pH value is 5.5

| No | Amino acid | Amino acid content, % wt | Fatty acid composition of lipids | Micro-nutrient elements |
|---|---|---|---|---|
| 1 | taurine | 0.020 | Myristinic acid C14:0 | Potassium |
| 2 | aspartic acid | 0.042 | palmitic acid C16:0 | Calcium |
| 3 | glutamic acid | 0.045 | palmitoleic acid C16:1 | Magnesium |
| 4 | Glycine | 0.030 | heptadienoic acid C17:2 | Iron |
| 5 | alanine | 0.017 | stearic acid C18:0 | Zink |
| 6 | cystine | 0.003 | oleic acid C18:1 | Copper |
| 7 | leucine | 0.031 | linolenoic acid C18:3 | Chrome |
| 8 | tyrosine | 0.0063 | eicosenoic acid C20:1 | Iodine |
| 9 | phenylalanine | 0.041 | arachidonic acid C20:4 | |
| 10 | gamma-aminobutyric acid | 0.002 | eicosapentaenoic acid C20:5 | |
| 11 | Ethanolamine | 0.003 | docosenoic acid C22:2 | |
| 12 | lysine | 0.018 | docosahexaenic acid C22:6 | |
| 13 | arginine | 0.023 | tricosatetraenoic acid C23:4 | |
| 14 | proline | 0.114 | tricosapentaenoic acid C23:5 | |

-continued

| No | Amino acid | Amino acid content, % wt | Fatty acid composition of lipids | Micro-nutrient elements |
|---|---|---|---|---|
| 15 | serine | 0.018 | tetracosenoic acid C24:1 | |
| 16 | histidine | 0.008 | docosenoic acid C22:2 | |
| 17 | threonine | 0.015 | | |
| 18 | valine | 0.012 | | |
| 19 | methionine | 0.006 | | |
| 20 | isoleucine | 0.014 | | |

Toxicity Studies of the Composition Based on Bivalve Molluscs

The objectives for the first stage of studies on the composition for parenteral administration, comprising 5% aqueous solution of the hydrolyzate produced in Example 1 (hereinafter referred to as composition A), included the following:

1. Toxicological and biological assays: definition of acute and subacute toxicity (including irritant and allergenic effects).
2. Estimation of embryotropic (embryotoxic and teratogenic) effects.
3. Possible subchronic toxicity testing in several animal species.

Materials and Methods

Experiments were carried out on 115 white rats and 55 white mice using existing pharmacological, toxicological, haematological, biochemical and immunological assays. Some techniques and schemes of toxicity studies of the preparation in laboratory animals and other animal models are provided throughout the disclosure of the experiments.

Experiments were carried out twice with statistical analysis of the results.

Determination of Acute and Subacute Toxicity (Including Irritant and Allergenic Effects)

Acute toxicity of composition A was measured by a single intramuscular administration of therapeutic dose 0.2 ml/animal, and of 2-fold increased and 4-fold increased doses, i.e. 0.4 and 0.8 ml/animal, that is 1600 and 3200 mg/kg. No apparent deviations in animal behavior were observed, rats took food and water willingly. According to toxicological classification, preparation having $LD_{50}$ higher than 1000 mg/kg belongs to low toxicity substances. For the composition being studied, this parameter exceeded the dose of 1000 mg/kg by several times.

To determine subchronic toxicity, the preparation in a dose of 0.2 ml/animal (or 800 mg/kg) was administered to rats continuously for 10 days. As well as in the acute experiments, no negative effects of the composition on animals were observed.

Irritation effects were estimated using epicutaneous application. Two groups of white rats with body weight 250-270 g were formed for estimation of possible irritative and allergenic effect of the composition. Each group consisted of 5 animals. For the first group, the composition for parenteral administration was applied for 20 days onto shaved areas on the backs (1.5×2 cm) and hips (1×0.5 cm), and onto conjunctiva of animals, while for the second group 0.9% sodium chloride solution was applied.

The following parameters were taken into account during the experiment: onset of conjunctival hyperaemia; cutaneous and palpebral edema, development of inflammation, skin reaction (erythema, rash) while using the preparations. Observations on experimental laboratory animals showed no allergenic and local irritant effects of the composition. No skin reaction manifesting as erythema or rash was observed on shaved areas on backs and hips.

Effects of the composition for parenteral administration and these of normal saline solution on eye mucosa and shaven back and hip areas of white rats are presented in Table 1.

TABLE 1

| Parameters | $1^{st}$ group | $2^{nd}$ group |
|---|---|---|
| Skin hyperemia | absent | absent |
| Cutaneous edema | absent | absent |
| Eyelids condition | unchanged | unchanged |
| Conjunctivitis | absent | absent |
| Keratitis | absent | absent |
| Lacrimation | absent | absent |
| Pain reaction | absent | absent |

The provided data show that the composition A does not have local irritant allergenic effect. Eye mucosa and eyelids of the white rats stayed in satisfactory condition, signs of inflammation, edema, skin hyperemia and lacrimation were absent and no pain reaction was observed after application of the solutions. Overall condition of the white rats was satisfactory; they were physically active and took food and water willingly.

Skin capillary permeability, considered as secondary endpoint for evaluation of the irritant effect, was measured by McClure-Aldrich test. The test consists in intracutaneous administration of 0.2 ml of physiological solution to experimental animals, into the area whereto the studied preparation was applied, and into symmetrical control area, on the $15^{th}$ day of experiment. Time of salt blister resorption in both areas was recorded. The studies showed that the preparations do not influence skin capillary permeability.

Definition of Embryotropic Effect of the Composition (Embryotoxic and Teratogenic)

Embryotoxic and teratogenic effects of the composition A were estimated according to guidelines published by A. G. Tretyakov (1988).

Possible embryotoxic effects of the preparation were tested on 15 pregnant female rats weighing 150-180 g, and 3 males of first and second generation. Males were introduced to females at estrus and proestrus at evening hours, one male for each 4 females. Detection of sperm in vaginal swabs the next morning was considered the first day of gestation. The studies began with administration of therapeutic dose of the composition—0.2 ml per capita. The composition was administered intramuscularly during the period from $1^{st}$ to $17^{th}$ day of gestation. Control animals were administered normal saline solution intramuscularly over the same period and in the same dosage.

Gestation course was surveyed by examination of vaginal swabs of the female rats on the days 4-5 after insemination and gestation course on gestation days 10 to 11 and by weighing the females on gestation days 1, 7, 14 and 20. On 20th day of gestation the females were decapitated; numbers of yellow bodies of pregnancy in ovaries and numbers of implantation sites was calculated.

To determine embryotoxic effects of the composition A, pre-implantation zygote death (difference between the number of yellow bodies of pregnancy in ovaries and number of implantation sites in uterus, to total number of yellow bodies), postimplantational fetal death (i.e., difference between the number of implantation sites and the number of alive fetuses in uterus, to the number of implantation sites) and total fetal mortality (difference between the number of yellow bodies of pregnancy and number of alive fetuses, as percents of the yellow bodies number in ovaries), were calculated.

No disorders during pregnancy were detected upon administration of composition A to pregnant rats in the dose of 0.2 ml per capita in said time points of embryogenesis and organogenesis (gestation days 1 to 17); animals took water and food willingly. Furthermore, no disorders were detected by examination of internal organs using Wilson's method and of skeletal system using Dawson's method.

Key parameters, i. e., preimplantation zygote death—equal to 1.90 in the test group and 2.3% in the control group, postimplantational fetal death—equal to 1.92 and 2.0%, respectively, total fetal mortality—equal to 3.3 and 3.46%, respectively, were close in value, indicative of no embryotoxic effects of the composition. Weight, size and number of fetuses and fetoplacental index in test and control groups were not statistically different and fell within physiological range. For example, mean number of fetuses per one female upon administration of the preparation was equal to 8.9±0.06 against 8.7±0.06 in the control group, weight equal to 2093.3±8.3 and 2010.2±5.1 mg and size equal to 2.7±0.9 and 2.7±0.1 cm, respectively.

Visual inspection and microscopic examination of internal organs by Wilson's method revealed no fetal malformations in rats which were administered the preparation (no external and internal abnormalities).

Microscopic examination of fetal skeletal bones by Dawson's method showed that the studied composition did not cause abnormalities in fetal skeletal system throughout the embryonic period.

The absence of fetal skeletal system abnormalities is confirmed by identical weights of test and control animals and fetoplacental indices (26.97 and 27.60, respectively).

It was established that composition A administered in a dose of 0.2 ml per capita daily throughout gestation ($1^{st}$ to $17^{th}$ day) was neither embryotoxic nor teratogenic. The animals tolerated daily administration of the composition well, and the data resulting from the study of materials obtained from them, i.e., weight and size of fetuses, condition of the internal organs and the skeletal system, were identical (in specific series, weight and size of fetuses and particular bones sizes were even greater) relative to that of control animals, that was further confirmed by probability levels equal to or higher than 0.05 (P 0.05).

Therefore, composition A does not cause second-generation embryotoxic and teratogenic effects in laboratory animals.

Local Farm Scale Tests on Possible Subchronic Toxicity of the Composition in Various Animal Species.

Experiments were carried out on cows, calves, weaner piglets and dogs.

Composition A was administered intramuscularly for the duration of 10 days in the following dosages: to cows—10 ml/animal; to calves (live weight 30-33 kg)—5 ml/animal; to piglets (live weight 9.3 kg)—2 ml/animal; to dogs (live weight 35-40 kg)—5 ml/animal.

Overall clinical condition, appetite and possible adverse events in animal behavior were considered during daily monitoring of the animals. Certain haematological and immunobiochemical parameters were measured in blood samples taken at the beginning and at the end of experiment. In piglets and calves, initial and final live weight was measured.

Tests on Cows. It was established that daily administration of the above composition to cows in a dose of 10 ml/animal did not adversely affect external behavior of the animals, which took their feeding ration and water as usual. No negative impact on the animals' behavior was revealed. Neither were statistically significant differences in erythrocytes count, WBC count and haemoglobin content revealed by haematological analyses. Biochemical analyses showed a certain decrease in carotin and total protein content in blood serum; however these changes were not significant. Concentrations of calcium and phosphorus in blood serum were within normal ranges, no variations of indices obtained prior to and at the end of the experiment were recorded. Administration of the composition had a beneficial effect consisting in possibility of an earlier (by 7-10 days) fertilization in 6 out of 10 experimental cows.

Tests on Calves. The composition was administered to calves immediately after birth. No adverse events in their behavior were observed. Conversely, only 3 out of 10 calves got diarrhea, though this ratio averages between approximately 67-75%. Blood analysis revealed that haematological parameters were almost the same before and after administration of the composition. As regards biochemical parameters, a trend toward increasing total protein levels was observed, though the difference was statistically non-significant. At the same time, the experimental calves had a higher body weight at the age of one month (51.3+2.1 kg against 50.1+2.7 kg in control calves), and recorded incidence of bronchopneumonia was lower in these animals.

Tests on Piglets. Composition A was injected to piglets 10-13 days before weaning. No deviations in piglets' behavior were observed. Neither were differences between initial and final data regarding formed elements count, and Ca and P levels, detected in blood. However, a trend toward increasing total protein content was observed, to manifest later in a 3.7±0.2% higher live weight as compared to control animals.

Tests on Dogs. Tests were conducted on dogs of middle age group (5-7 years). It was found that intramuscular administration of composition A in the dose of 5 ml/animal over 10 days had no negative impact on dogs' behavioral reactions. The animals took food and water willingly. Furthermore, haematological parameters did not change throughout the experiment.

The above described studies on laboratory and livestock animals confirmed low toxicity of the composition A, in particular, lack of embryotropic effect.

EXAMPLE 3

Immunostimulative, Adaptogenic, Growth-promoting and Wound Healing Effects of Composition A Materials and Methods Tests were conducted on 84 white rats and 36 white mice using pharmacological, haematological, biochemical and immunologic assays known in the art. Upon studying beneficial effects of composition A on the organisms of laboratory animals, certain haematological and immunobiological indices of the test and control animals were considered. Haematological parameters were evaluated in blood specimens by methods known in the art: white blood cells count per 1 cubic millimeter using Gorjaev's chamber. The following immunobiological indices were counted: blood protein content, glucose, phagocytosis and a number of other parameters, characterizing condition of an organism. The total protein content in blood serum was measured by refractometric analysis. Refractive index of blood serum depends mainly on the amount of proteins.

Glucose concentration was measured using the ortho-toluidine method based on staining of glucose compound with ortho-toluidine in acetic acid solution, the intensity of said being proportional to the glucose concentration.

Immunoglobulin G content in blood serum was measured using Mancini's method (1965) in modification by L. S. Kolabskaya et al. (1975). This method consists in formation of precipitin ring as the result of interaction of the mixture of agar and immunoglobulin antiserum with antigen of the studied serum, introduced into wells of an agar plate. Precipitate area, as a squared ring diameter, is directly proportional to the antibodies concentration in agar. In this case, the concentration of the test antigen and the precipitate area are linearly dependent.

Study of phagocytic activity is based on in vitro evaluation of the peripheral neutrophils capacity (opsonophagocytosis assay, OPA) in tested animals to phagocytize (to engulf) microbial cells. White *Staphylococcus* Staph. albus is employed as a test culture for OPA.

The intensity of phagocytosis was measured on the basis of phagocytic activity (PA), phagocytic number (PN) and phagocytic index (PI).

Phagocytic activity (PA) is a percentage of phagocytizing neutrophils in total neutrophil count. Phagocytic index (PI) is a number of engulfed microbial cells (m.c.) per one neutrophil, in total neutrophil count. Phagocytic number (PN) is a number of microbal cells in one active (phagocytizing) neutrophil.

The tests were repeated twice and the results obtained were statistically analysed.

3.1 Immunostimulative Effect

Composition A was administered intramuscularly to experimental white rats (three groups, each consisting of 6 animals) over 5 days in a dose of 0.2 ml/animal. Blood phagocytic index (PI), phagocytic activity (PA) and phagocytic number (PN) and immunoglobulins A and G for immunological parameters (Tables 2, 3) were evaluated. Phagocytic activity provided by the composition was compared to that of the well-known immunomodulator evinton. Evinton is comprised of: Thuja D6, Vincetoxicum D4, Echinacea purpurea D4 and normal saline solution.

TABLE 2

| Groups of animals | Phagocytic index | Phagocytic activity | Phagocytic number |
|---|---|---|---|
| Composition A | 8.2 ± 1.42 | 50.0 ± 1.24 | 19.6 ± 1.47 |
| Evinton | 10.0 ± 1.34 | 60.0 ± 1.45 | 15.33 ± 1.29 |
| Control | 6.72 ± 1.87 | 33.33 ± 1.39 | 8.0 ± 1.64 |

TABLE 3

| Groups of animals | Immunoglobulin A | Immunoglobulin G |
|---|---|---|
| Composition A | 2.99 ± 0.59 | 8.06 ± 1.57 |
| Evinton | 2.9 ± 0.62 | 7.42 ± 1.32 |
| Control | 1.85 ± 0.37 | 6.85 ± 0.32 |

The obtained results indicate that the use of the composition promotes the increase in phagocytic activity of neutrophils relative to the control group; also, production of immunoglobulin G was somewhat higher relative to the effect of Evinton and to the control group of white rats.

Thus, composition A has a certain immunostimulatory effect on test animals organisms and increases cellular and humoral immunity indices.

3.2. Adaptogenic (Antistress) Properties

The test was conducted on 12 rats, 4 animals being in each of three groups. Stress in experimental white rats was induced using a shaking machine simulating transport (physical) stress. The box with animals was placed onto the shaker and held atop the operating machine for 30-40 min. The most informative parameters, characterizing the onset and development of stress response (stress mediators): glucose, total protein and leukocytes (WBC) levels, were measured in blood of the white rats.

Composition A was administered to the animals of the $1^{st}$ group intramuscularly 3 days previous to stress induction in a dose of 0.2 ml. 2.5% solution of neuroleptic agent aminazin in a dose of 0.5 mg per capita was administered to the animals of the $2^{nd}$ group. A normal saline solution was administered intramuscularly to the animals of the $3^{rd}$ (control) group. Rats' blood examination to estimate the above parameters was performed 1 h and 24 h after stress induction.

Laboratory data indicate that glucose and WBC levels increase and total protein content decreases under stress.

By way of example, glucose concentration in the group receiving composition A was 4.97±0.1 mmol/L against 6.46±0.45 mmol/L in the group receiving aminazin and 10.0±0.7 mmol/L in the control group as early as 1 h after stress induction. This variable increased to 5.42±0.2 mmol/L, 6.25±0.3 mmol/L and 8.33±0.4 mmol/L, respectively, 24 hours after stress induction. Values of laboratory blood tests 1 h and 24 h after stress induction are represented in Tables 4 and 5, respectively.

TABLE 4

Haematological parameters 1 hour after stress induction

| Group | Glucose mmol/L | Total protein, g/L | Leukocytes (WBC), $10^3$/uL |
|---|---|---|---|
| Composition A | 4.97 ± 0.1 | 67.5 ± 1.2 | 5.6 ± 1.7 |
| Aminazin | 6.46 ± 0.45 | 66.0 ± 0.5 | 4.3 ± 0.4 |
| Isotonic NaCl solution (Normal saline solution) | 10.0 ± 0.7 | 66.0 ± 0.9 | 5.8 ± 0.52 |

TABLE 5

Haematological parameters in white rats 24 hours after stress induction

| Group | Glucose, mmol/L | Total protein, g/L | Leukocytes (WBC), $10^3$/uL |
|---|---|---|---|
| Composition A | 5.42 ± 0.2 | 72.7 ± 2.3 | 5.6 ± 0.1 |
| Aminazin | 6.25 ± 0.3 | 72.4 ± 1.6 | 6.1 ± 0.3 |
| Normal NaCl solution | 8.33 ± 0.4 | 66.2 ± 2.5 | 7.05 ± 0.2 |

3.3. Study of Growth-promoting Effect

The influence of composition A on growth and development of the laboratory animals was studied on 18 white mice weighing 19-23 g. 3 groups, each consisting of 6 animals, were formed. "Evinton>>, a complex homeopathic preparation for animals, was used as a comparative agent. All animals were weighed before and after the experiment. At the end of the experiment, specimens of blood were taken for clinical and immunobiochemical analysis. During the experiment, which lasted for 15 days, the animals did not show signs of anxiety, took food and drank water willingly. The highest mobility was observed in animals of the test group, which were administered a dose of 0.1 ml of composition A per capita subcutaneously. Animals of the comparison group were administered a dose of 0.1 ml of complex homeopathic preparation for animals "Evinton>> per capita subcutaneously. A normal saline solution was administered in a dose of 0.1 ml per capita subcutaneously to the control group. Course of administration of the preparations was 3 days.

The best values of weight gain relative to control animals were obtained upon using composition A. The data are represented in Table 6.

TABLE 6

Growth-promoting effect of the preparations

| Groups of animals | Body weight before experiment (g) | Body weight by the end of experiment (g) | Weight gain within 10 days (g) | Weight gain relative to controls (%) |
|---|---|---|---|---|
| Composition A | 25.75 ± 0.692 | 32.0 ± 0.75 | 6.25 ± 0.62 | 113.6 |
| Evinton | 24.75 ± 0.56 | 30.75 ± 0.56 | 6.0 ± 0.56 | 105.1 |
| Control | 21.5 ± 1.19 | 27.0 ± 1.4 | 5.5 ± 1.34 | 100.0 |

3.4. Study of the Composition's Wound Healing Activity

Wound healing goes through three main phases: inflammation, regeneration, and remodeling of the scar and epithelialization. Sluggish wound process with a slow growth of granulations and delayed epithelialization may occur at any phase of healing.

For estimation of the wound healing effect of composition A, tests were conducted on 6 rats, weighting 250 g, each group consisting of 4 animals. Back areas 2×2 cm were theretofore shaven, dehaired skin being cleaned of impurities; then, the skin was grasped with surgical forceps and a 1 cm long scalpel incision was made.

The progress of experimental wound healing was evaluated by the following parameters:
1. Visual observations
   time point when granulations appear in the wound
   closure of the wound bed by granulation
   filling of the wound chamber with granulations
   quality of the granulations
   progress of epithelialization
   condition of tissues surrounding the wound.
2. Recording wound area changes.
3. Scab shedding was considered to be the time of completed wound healing.

During the experiment, composition A was administered to the test group intramuscularly in therapeutic dose of 0.2 ml per capita over 4 days. Control animals were administered normal saline solution intramuscularly in the same dosage over the same period.

Granulations appeared in the wounds on the $2^{nd}$ day in both groups, the wound bed closure and filling of the wound chamber with granulations in both the test and the control groups was observed on the 5th day from the beginning of the experiment. In the course of the experiment, wound area contraction by 0.3 cm was observed in the test group on the 4th day; no wound area contraction was observed during this period in the control group.

The duration of complete wound healing was 6 days in the test group and 8 days in the control group.

The above studies have revealed a number of pharmacological benefits of composition A such as immunostimulative, adaptogenic, growth-promoting and wound healing effects. Recommendations on use of composition A for increasing productivity and natural resistance of animal organism were developed on the basis of the undertaken studies and the results obtained.

Clinical data obtained in laboratory animal models provided the basis for the tests on livestock and domestic animals, the results of which are given below.

EXAMPLE 4

Influence of the Composition on Leucogram and Bone Metabolism in Blood of the Nursery Piglets Tests were conducted for 2 weeks on piglets aged 45 and 65 days (n=15) kept in the conditions of a pigsty. There were 2 groups of animals: the test group of animals to which composition A was administered intramuscularly once per 24 hours in the dose of 2 ml per capita, every other day over 14 days, and the control group of animals not getting special treatment. Animals were recruited into groups according to an analogue method.

The results of studying the effects of the composition on electrolyte exchange and bone metabolism in piglets' blood are represented in Table 7.

TABLE 7

| No II/II | Variable | Units | Control group Before experiment | Control group After experiment | Test group Before experiment | Test group After experiment |
|---|---|---|---|---|---|---|
| 1. | calcium | mmol\L | 2.32 ± 0.3 | 2.4 ± 0.5 | 2.52 ± 0.5 | 2.4 ± 0.6 |
| 2. | phosphorus | mmol\L | 1.83 ± 0.3 | 1.78 ± 0.5 | 1.76 ± 0.3 | 1.84 ± 0.27 |
| 3. | alkaline phosphatase | IU\L | 87.8 ± 7.8 | 86.2 ± 5.5 | 60.9 ± 2.7 | 39.5 ± 1.2 |

The following conclusion can be derived from the research results: piglets of the control group exhibit imbalance of calcium:phosphorus ratio, as well as increased levels of alkaline phosphatase, that may indicate (regardless of age-related changes) inflammatory processes affecting intestinal mucosa, juvenile osteodystrophy, rickets-like conditions.

Improvement was recorded after two weeks of application of the composition in piglets of the test group relative to the control group: appetite back to normal, animals more active.

Biochemical variables dynamics was the following: alkaline phosphatase level decreased by 35.1%, calcium and phosphorus levels came close to physiological range in contrast to animals of the control group, not exhibiting changes of said biochemical parameters.

Therefore, use of composition A promotes normalization of calcium-phosphorus metabolism and thus it can be recommended for use in combined treatment of osteo-articular pathologies.

The results of studying the composition influence on weaner piglets' blood leucogram are shown in Table 8.

TABLE 8

| Parameter | Units | Reference Range | Control group Before experiment | Control group After experiment | Test group Before experiment | Test group After experiment |
|---|---|---|---|---|---|---|
| Leukocytes (WBC) | thous/uL; $10^9/\Pi$ | 8.7-37.9 | 10.9 ± 1.2 | 15.1 ± 2.1 | 11.05 ± 1.6 | 16.1 ± 2.5 |

TABLE 8-continued

|  |  |  | Control group | | Test group | |
| --- | --- | --- | --- | --- | --- | --- |
| Parameter | Units | Reference Range | Before experiment | After experiment | Before experiment | After experiment |
| Juvenile neutrophils | % | 0-2 | 0.15 ± 0.02 | 0.17 ± 0.01 | 0.14 ± 0.02 | 0.17 ± 0.12 |
| Band neutrophils | % | 2-4 | 1.9 ± 0.04 | 1.01 ± 0.011 | 1.85 ± 0.3 | 3.5 ± 0.7 |
| Segmento nuclear neutrophils | % | 40-48 | 65.45 ± 12.1 | 59.21 ± 9.8 | 64.3 ± 14.4 | 55.2 ± 8.9 |
| Eosinophils | % | 1-3 | 0.8 ± 0.01 | 0.9 ± 0.012 | 0.85 ± 0.03 | 1.6 ± 0.04 |
| Basophils | % | 0-1 | 0.7 ± 0.013 | 0.78 ± 0.01 | 0.73 ± 0.13 | 1.3 ± 0.3 |
| Monocytes | % | 2-6 | 3.5 ± 0.24 | 4.2 ± 0.9 | 3.6 ± 0.23 | 3.1 ± 0.07 |
| Lymphocytes | % | 40-50 | 27.5 ± 3.1 | 32.73 ± 3.6 | 28.53 ± 4.7 | 37.13 ± 4.9 |

These findings display the reduction of lymphocytes, basophils and eosinophils in piglets, whilst levels of segmented neutrophils are increasing; these alterations may be indicative of protective and adaptive response to stress in animal organisms. Improvement was recorded after two weeks of application of the composition in piglets of the test group in contrast to these of the control group: appetite back to normal, animals behave more actively. Haematological parameters were closer to physiological values in the test group relative to the control group. Therefore, composition A can be recommended for combined corrective treatment of postweaning stress in livestock.

EXAMPLE 5

Study of Detoxifying Properties of the Composition 17 dogs with acute piroplasmosis confirmed by presence of *Babesia* parasites in peripheral smears were followed up. Condition of all animals was regarded as severe: rectal temperature up to 41.0° C., mucous membranes pale and icteric, dark urine with blood, decreased appetite down to food refusal, gait disorders, general weakness; in some cases, fainting.

Piro-Stop ("ПИро-СтоП") drug was employed as a specific therapy (twice, intramuscularly, at 24 hour intervals). Composition A was used in an amount 5-15 ml (depending on animal weight) intravenously (by stream infusion) once every 24 hours in addition to conventional therapy (Ringer-Lockes solution intravenously, 60 drops/min, 10-15 ml/kg 2 times per 24 hours, heart preparations). In most severe cases the preparation was administered 2 times per 24 hours intravenously during first 2-3 days, followed by single intramuscular administrations every 24 hours.

It was observed that the use of the above composition substantially increased the treatment efficacy relative to conventional therapy. For example, the overall condition of all patient animals improved significantly as early as 3-5 hours after the very first administration of the composition. The animals regained appetite quickly, body temperature and cardiac rate being decreased. In all dogs, haemoglobin values returned to normal by the end of the 2$^{nd}$ week from the beginning of treatment.

Detoxification effect of the above composition is due to hepatoprotective properties, as confirmed by the results of liver function dynamic analysis in sick animals. Normalization of ALT, AST, albumin, GGT, globulin, total protein, prothrombin and alkaline phosphatase levels, and positive dynamics of total bilirubin and indirect bilirubin fraction and amylase levels were observed upon even a single intravenous administration of the composition.

Thus, the composition of the present disclosure has a strong detoxifying effect, in particular due to its hepatoprotective properties.

EXAMPLE 6

Influence of the Composition on Musculoskeletal System in Dogs

Composition A was used as a mono- and complex therapy in dogs with age-related changes of musculoskeletal system. The group consisted of 5 dogs with normal and excess weight. The core symptoms manifested in animals as apathy, absence of appetite, refusal to walk, lameness of varying severity and various pain syndromes. The examination of the animals' joint stiffness, pain reaction to spine palpation (thoracic and lumbar regions). Radiographs revealed various degrees of hip joint arthrosis and spine osteochondrosis.

Three Russian hunting sighthounds aged 13 years and weighting approximately 25 kg (normal) were administered a dose of 5 ml of the composition, comprising 5% aqueous solution of the hydrolyzate derived from bivalve molluscs meat, intramuscularly, every other day, for a total of 15 injections.

The above composition was prescribed to the Airedale terrier aged 12 years (female), suffering from overweight with spine tenderness, in a dose of 4 ml intramuscularly every other day in an amount of 10 injections. The above composition was prescribed to the English bulldog aged 10 years, suffering from obesity and lack of activity, as part of complex therapy: 4 ml intramuscularly every other day, for a total of 10 injections, 2 ml of bonharen intravenously once a week in the amount of 4 injections, 10 ml of Kynosil once a day over 2 months. Specimens of blood were collected from dogs for clinical and biochemical analyses before and after administration of the preparations. After the course of treatment, the animals' condition has changed drastically: in all dogs, appetite restored, physical activity increased, alkaline phosphatase levels fell from excess to normal, alanine transaminase (ALT) decreased, urea level increased while staying within normal range; taken together, all these indicate beneficial effects of composition A on the condition of musculoskeletal system and liver function.

EXAMPLE 7

Treating Pathological Conditions in Dogs

Provided hereafter are the results of using composition A in treating various pathologies in dogs.

1). English Bulldog
Age: 1 year and 3 months
Weight: 30 kg

Diagnosis: demodecosis, urine acid diathesis, streptoderma: areas affected are the entire head, cheeks, forehead, areas between and behind ears, all covered in purulent crust, moist eczema.

Treatment regime: common symptomatic treatment, and Composition A in the dose of 3 ml intramuscularly, once a day for 5 days.

Results in a week: dry, healing skin; edema and itching absent, no pus. Clean healing skin.

2). Dobermann
Age: 2 years 6 months
Weight: 23 kg

Diagnosis: Severe leanness despite good nutrition and no helminthes or parasites. Dandruff on skin, bilirubin in urine.

Treatment regime: Composition A in the dosage of 5 ml, i.m., once a day, for 5 days.

Results in a month: weight gain 2 kg, bilirubin is normal, hair clean and shiny.

3). American Bulldog
Age: 5 years
Weight: 60 kg

Diagnosis: Leptospirosis. Symptoms: otopyosis, bloody diarrhea, vomiting.

Treatment regime: Drip infusion and symptomatic treatment, as well as composition A in the dose of 5 ml i.m. once a day, for 5 days.

Results: vomiting and diarrhea stopped within 2 days, clinical blood and urine were back to normal within a week after initiation of treatment. No relapse was observed within 4 months.

4). Dalmatian dog
Age: 1 year and 7 months
Weight: 22 kg

Diagnosis: Trichophytia accompanied by allergic dermatitis. The entire back and sides affected.

Treatment regimen: symptomatic treatment.

Treatment for a month was ineffective.

Treatment regimen: 5 injections of composition A, each 3 ml, i.m., every second day.

Results after two weeks: all symptoms disappeared, clean hair.

5). Yorkshire terrier
Age: 1.5 months
Weight: 1 kg

Diagnosis: Combined revaccination was done one week before its due time; temperature of 41.6, bronchopneumonia, unilateral purulent discharge from the eyes and nose 4 days later.

Treatment regimen: symptomatic treatment and 1 ml of Composition A 5:0, i.m., once a day, for 5 days.

Results after two days: body temperature back to normal, purulent discharge and lung rales are absent.

6). Kurzhaar (German shorthaired pointer)
Age: 12 years
Weight: 17 kg

Diagnosis: Chronic leptospirosis. Body temperature of approximately 40 degrees over the period of two months, tenderness of liver and kidneys, cachexia, dandruff, skin odour, hardly walks, appetite absent. Conventional therapy is ineffective.

Treatment regimen for the first week: high doses of antibiotics; symptomatic treatment. Clinical blood count normalized, but all the symptoms continued.

Treatment regimen: Withdrawal of antibiotics, symptomatic treatment of liver and kidney; Composition A in the dose of 3 ml i.m. once a day for 5 days.

Results after two days: body temperature back to normal, state of the liver and kidneys improved within 3 weeks, dandruff disappeared, hair coat and appetite improved.

Relapse two months later: infectious arthritis—two injections of the composition, each 3 ml, i.m., once a day.

All symptoms were gone.

EXAMPLE 8

Canine Piroplsmosis: Comparative Study of the Present Composition with Oral Conventional Products The present example demonstrates the effectiveness of the present composition administered parenterally to dogs suffering from piroplasmosis as compared to oral administration of conventional products The study includes 45 dogs suffering from piroplasmosis. In addition to clinical signs, diagnostics included examination of peripheral blood smears for the presence of *Babesia*.

The dogs suffered from severe piroplasmosis symptoms including rectal temperature 39.7-41,0° C., dark bloody urine, reduced appetite, food refusal, pale mucous membranes, general weakness, in some cases fainting and gait failure disorders.

As a general therapy the dogs were administered PiroStop intramuscularly (by weight, twice during 24 hours) along with Ringer-Lockes solution (I.V., 60 drops per minute, 10-15 ml/kgB.I.D.), and cardiovascular supportive drugs.

Further the dogs were uniformly divided into 3 groups including

Group 1: animals receiving the above-identified general therapy,

Group 2: animals administered 10-30 ml (depending on body weight) of the composition comprising sea mussels undiluted hydrolizate 1-2 times per day orally, in addition to the general therapy, Group 3: animals administered 5-15 ml (depending on animal's body weight) of the composition representing 5% aqueous solution of the hydrolizate via intravenous infusion, 1-2 times daily, in addition to the general therapy.

The selection of animals in each group was made with maximum possible uniformity taking a general condition, age, body weight, and breed of the dogs into account.

As a result of the therapy no statistically significant difference in animals' condition and duration of recovery was revealed between Groups 1 and 2. The number of deceased animals was 3 in Group 1, and 2 in Group 2, all of the animals surviving in Group 3.

In Group 3, dogs with severe symptoms were treated via intravenous administration two times a day over the first 2-3 days followed by daily intramuscular administration. The general condition of the affected animals was found to improve significantly in 3-5 hours after initial infusion of the composition. Animals having the disease of moderate and mild severity regained appetite. The dogs experienced rapid reduction of toxicity reactions. Haemoglobin parameters were back to normal in all of the dogs within about 3 weeks. The clear reduction of intoxication symptoms is observable immediately after its intravenous administration. Beneficial effect on main parameters of animals' liver function was shown over the course of the composition application. Normalization of ALAT, AAT, albumine, GGT, globulins, total protein, prothrombin and alkaline phosphatase levels was observed. Further, the improvement of total bilirubin and indirect bilirubin fraction as well as amylase was observed.

On the other hand, haemoglobin parameters and normalization of ALAT, AAT, albumin, GGT, globulins, total protein, prothrombin and alkaline phosphatise levels occurred significantly later (in 6-14 days) in animals of Groups 1 and 2 as compared to Group 3. The dogs in Group 2 and 3 was getting back to normal condition unevenly and there was a long-lasting lack of appetite. Physical condition recovery after the formal recovery took 1-2 months longer in animals of Group 1 and Group 2 as compared to the animals of Group 3.

EXMAPLE 9

Improvement of Reproductive Function in Cows

The present example illustrates the method of improving reproductive function in cows. More specifically the present example demonstrates the effectiveness of the present composition administered via injection to cows suffering form ovarian hypofunction as compared to oral administration of conventional products.

Low efficiency of insemination in cows is a problem of current concern in the farms of Northwest Russia. This can be explained by various reasons varying from housing and feeding conditions to semen material quality. The ratio of cows diagnosed with ovarian hypofunction in a number of farms is up to 70%.

A study was performed to estimate the influence of the present composition on insemination efficiency in cows suffering from ovarian hypofunction.

The cows were divided into 3 groups.

Group 1: a control group;

Group 2: animals receiving oral administration of a hydrolizate produced from sea mussels;

Group 3: animals receiving the composition representing 5% aqueous solution of the hydrolizate via intramuscular injections.

Each group included 20 cows uniformally selected on the basis of age, intensity of the identified ovarian hypofunction and time of last calving. Artificial insemination was conducted according to standard well-proven procedure in all groups for the first time immediately after oestrus confirmation and for the next time at 12 hours thereafter.

Group 1 did not receive any medication. The animals of Group 2 were given to drink the preparation twice including 20 ml immediately after oestrus confirmation (prior to the first insemination), and then immediately after the second insemination. The animals of Group 3 received a first intramuscular injection of 10 ml immediately after oestrus confirmation (prior to the first insemination), and the second intramuscular injection of 10 ml immediately after the second insemination.

As a result, Group 1 was found to comprise 12 calvers, Group 2 was found to comprise 12 calvers, and Group 3 was found to comprise 17 calvers.

The results of the present example demonstrate that the oral administration of the conventional hydrolizate has no substantial influence on animal condition and reproductive function. However use of the injectable composition according to the present invention results in a rapid detoxification and recovery of haematological parameters, and reduces lethality rates for canine piroplasmosis as well as improves reproductive function in cows having ovarian hypofunction.

The embodiments described hereinabove are further intended to explain best modes known of practicing it and to enable others skilled in the art to utilize the disclosure in such, or other, embodiments and with the various modifications required by the particular applications or uses. Accordingly, the description is not intended to limit it to the form disclosed herein. Also, it is intended that the appended claims be construed to include alternative embodiments.

The invention claimed is:

1. A method of improving reproductive dysfunction of a mammal in need thereof by administering via injection to said mammal an effective amount of a composition comprising
    (1) about 1 to 10% wt of a hydrolyzate obtained by enzymatic hydrolysis and/or acid hydrolysis from bioresources, said bioresources selected from the group consisting of floaters (*Anodonta*), Unio freshwater mussels (*Unio*), oysters (Ostreidae), mussels (Mytilidae), *tridacna* (*Tridacna*), pearl-oysters (*Pinctada*), scallops (Pectinidae), shipworms (Teredinidae), geoduck (*Panopea abrupta*), and ocean quahog (*Arctica Islandica*); and
    (2) water.

2. The method according to claim 1, wherein the composition is administered in the amount of 0.05 to 10 ml per 1 kg of a body weight of said mammal, from 1 to 5 times during 24 hours, over total period ranging from 1 to 50 days.

3. The method according to claim 1, wherein the composition is administered once in the amount of 0.05 ml to 10 ml per 1 kg of a body weight of said mammal.

4. The method according to claim 1, wherein said composition is injected subcutaneously, intracutaneously, intramuscularly or intravenously.

5. The method of claim 1, wherein water represents sterile water for injection.

6. The method of claim 1, wherein said mammal is a human.

7. The method of claim 1, wherein the mammal is a livestock animal.

* * * * *